United States Patent
Dallemer et al.

(12)

(10) Patent No.: US 6,635,781 B1
(45) Date of Patent: Oct. 21, 2003

(54) METHOD FOR HEMIHYDROGENATING DINITRILES TO FORM AMINONITRILES

(75) Inventors: Frédéric Dallemer, Lyons (FR); Aline Seigneurin, Le Chesnay (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 09/937,761

(22) PCT Filed: Mar. 29, 2000

(86) PCT No.: PCT/FR00/00787

§ 371 (c)(1),
(2), (4) Date: Jun. 7, 2002

(87) PCT Pub. No.: WO00/59870

PCT Pub. Date: Oct. 12, 2000

(30) Foreign Application Priority Data

Mar. 30, 1999 (FR) .............................. 99 04206

(51) Int. Cl.$^7$ ............................................ C07C 255/00
(52) U.S. Cl. ....................................... 558/459
(58) Field of Search .......................... 558/459

(56) References Cited

U.S. PATENT DOCUMENTS

| 2,967,200 | A | * | 1/1961 | Foster et al. | |
|---|---|---|---|---|---|
| 3,127,356 | A | * | 3/1964 | Hamilton et al. | |
| 3,898,286 | A | * | 8/1975 | Drake | 260/583 |
| 4,259,262 | A | * | 3/1981 | Drake | 564/491 |
| 4,302,604 | A | * | 11/1981 | Marwil | 564/491 |
| 4,536,347 | A | | 8/1985 | Horner et al. | |
| 5,512,697 | A | | 4/1996 | Schnurr et al. | |
| 5,756,808 | A | * | 5/1998 | Flick et al. | 558/459 |

FOREIGN PATENT DOCUMENTS

EP  0 077 911 A  5/1983

* cited by examiner

Primary Examiner—Joseph K McKane
Assistant Examiner—Robert Shiao
(74) Attorney, Agent, or Firm—Burns, Doane, Swecker & Mathis, L.L.P.

(57) ABSTRACT

A process is provided for the hemihydrogenation of dinitriles to corresponding aminonitriles using hydrogen in the presence of a supported catalyst. The supported catalyst comprises ruthenium supported on a carbon black, called acetylene black, resulting from the pyrolysis of paraffin oils.

17 Claims, No Drawings

METHOD FOR HEMIHYDROGENATING DINITRILES TO FORM AMINONITRILES

The present invention relates to the hemihydrogenation of dinitriles to corresponding aminonitriles.

The hydrogenation of dinitriles is generally carried out in order to prepare the corresponding diamines; thus, particularly, the hydrogenation of adiponitrile results in hexamethylenediamine, which is itself one of the base monomers in the preparation of polyamides.

However, it can sometimes prove necessary to prepare not the diamine but the intermediate aminonitrile. This is the case, for example but not limitingly, in the hemihydrogenation of adiponitrile to aminocapronitrile, which is capable of subsequently being converted either to caprolactam, the base monomer in the manufacture of polyamide-6, or directly to polyamide-6.

Thus, U.S. Pat. No. 4,389,348 discloses a process for the hydrogenation of dinitrile to ω-aminonitrile by hydrogen in ammonia and aprotic solvent medium in the presence of rhodium deposited on a basic support.

U.S. Pat. No. 5,151,543 discloses a process for the partial hydrogenation of dinitriles to aminonitriles in a solvent in molar excess of at least 2/1 with respect to the dinitrile, comprising liquid ammonia or an alkanol comprising an inorganic base which is soluble in the said alkanol, in the presence of a catalyst of Raney cobalt or nickel type.

U.S. Pat. No. 5,756,808 also discloses a catalytic process for the hemihydrogenation of dinitriles to aminonitriles. The catalysts disclosed are based on nickel, cobalt, iron, ruthenium or rhodium and are optionally used in combination with other elements known as promoter elements, such as palladium, platinum, iridium, osmium, copper, silver, gold, chromium, molybdenum, tungsten, manganese, rhenium, zinc, cadmium, lead, aluminium, tin, phosphorus, arsenic, antimony, bismuth and the elements belonging to the rare earth metals group. This document also specifies that ruthenium, in combination or not in combination with rhodium, can be used without promoter elements. The catalysts are deposited on supports, such as alumina or silica. The degrees of selectivity for aminocapronitrile (ACN) are between 70% and 80%.

However, in order to obtain an industrial process for the preparation of aminonitrile by hemihydrogenation of a dinitrile, it is necessary to obtain even higher selectivities for aminonitrile for degrees of conversion of the dinitrile in the region of 100% and therefore to find novel catalytic systems and to find processing conditions for the hemihydrogenation which make it possible to reach or to come close to this objective.

One of the objects of the present invention, which relates to the preferential hydrogenation of a single nitrile functional group of a dinitrile (called hemihydrogenation in the present text), so as to prepare predominantly the corresponding aminonitrile and only to a minor extent the diamine, is in particular to provide a novel catalytic system which makes it possible to improve the degree of selectivity of this reaction.

More specifically, the invention relates to a process for the hemihydrogenation of aliphatic dinitriles to corresponding aminonitriles using hydrogen in the presence of a catalyst of the type comprising a catalyst deposited or adsorbed on a support, characterized in that the catalyst is based on ruthenium, the support being a charcoal obtained by pyrolysis of a paraffin oil. These charcoals are also known as acetylene black, which terminology will be used in the continuation of the text.

Thus, these acetylene blacks exhibit a lower specific surface than that of the active charcoals generally used as catalyst support.

This specific surface is generally between 50 and 100 $m^2/g$. These acetylene blacks are also distinguished by other technical characteristics, such as their crystalline structure, their oxidation state, a high chemical purity and a high porosity.

Mention may be made, by way of example, as acetylene blacks which are suitable for the invention, of the blacks sold by the company SN2A under the trade names Y70, Y200, Y50 or YS.

The amounts of catalytic phases present on the support correspond to the amounts conventionally deposited in supported catalytic systems.

The use of the specific support of the invention makes it possible to obtain a high selectivity for aminonitriles for high degrees of conversion of the dinitriles. This level of selectivity cannot be achieved by using other conventional supports, such as alumina, silica or active charcoals generally of vegetable origin.

Thus, the use of this catalytic system makes it possible to achieve a degree of selectivity for aminonitriles of at least 80% for a degree of conversion of the dinitrile of greater than 60%. This degree of selectivity is greater than that obtained with a Raney nickel catalyst.

According to a novel preferred characteristic of the invention, the catalyst can be subjected to reduction by a reducing agent, such as hydrogen, for example, before introduction into the reaction mixture.

According to another embodiment of the invention, the catalyst comprises doping elements, at least one of which is iron.

The presence of these doping elements, in particular of iron, makes it possible to increase the lifetime of the catalyst and therefore the savings in the hemihydrogenation process.

The concentration of doping element with respect to the ruthenium is between 5% and 60% by weight, preferably between 10 and 30% by weight.

The doping elements other than iron which are suitable for the invention are chosen from the group comprising tungsten, manganese, rhenium, zinc, cadmium, lead, aluminium, tin, phosphorus, arsenic, antimony, bismuth, silicon, titanium, zirconium, the rare earth metals, palladium, platinum, iridium, osmium, copper, silver, chromium and molybdenum.

The aliphatic dinitriles which can be employed in the process of the invention are more particularly the dinitriles of general formula (I):

NC—R—CN (I)

in which R represents a linear or branched alkylene or alkenylene group having from 1 to 12 carbon atoms.

Use is preferably made, in the process of the invention, of dinitriles of formula (I) in which R represents a linear or branched alkylene radical having from 2 to 6 carbon atoms.

Mention may in particular be made, as examples of such dinitriles, of adiponitrile, methyl-glutaronitrile, ethylsuccinonitrile, malononitrile, succinonitrile and glutaronitrile and their mixtures, in particular the mixtures of adiponitrile and/or of methylglutaronitrile and/or of ethylsuccinonitrile which are capable of originating from the same process for the synthesis of adiponitrile.

The preferred compound of the invention is adiponitrile which makes it possible to obtain a precursor of polyamide-6 or of its monomer, caprolactam.

According to a preferred embodiment of the invention, the hemihydrogenation reaction is carried out in the presence of ammonia. This characteristic makes it possible to improve the performance of the catalytic system of the invention, in particular its lifetime.

According to another preferred characteristic of the invention, the hemihydrogenation of a dinitrile to aminonitrile can be carried out in the presence of a strong inorganic base deriving from an alkali metal element, from an alkaline earth metal element or from the ammonium cation.

Thus, the strong inorganic base is generally composed of alkali metal or alkaline earth metal hydroxides, carbonates and alkoxides or of hydroxides, carbonates and alkoxides of the ammonium cation. It is preferably chosen from alkali metal hydroxides, carbonates and alkoxides.

Preferably, the strong inorganic base employed is chosen from the following compounds: LiOH, NaOH, KOH, RbOH, CsOH, compounds comprising a quaternary ammonium radical and mixtures of these compounds. In practice, use is generally made of NaOH and KOH.

These strong bases are present in the reaction mixture according to a concentration of between 0.1 and 50 mol of $OH^-$ per kg of catalytic system, preferably between 5 and 35 mol of $OH^-$ per kg of catalytic system. In addition, this concentration is much lower, indeed even zero, when the hydrogenation is carried out in the presence of ammonia.

The composition of the hydrogenation reaction mixture is variable and depends in particular on the method of carrying out the hydrogenation.

This is because, if the process is carried out batchwise, the initial reaction mixture gradually becomes richer in aminonitrile and, to a lesser proportion, in diamine, whereas the concentration of dinitrile can either decrease, if all or most of the said dinitrile is charged at the beginning of the hemihydrogenation, or can remain relatively constant, if the dinitrile is introduced gradually during the reaction.

In contrast, if the process is carried out continuously, the average composition of the reaction mixture is substantially constant, apart from the periods during which the plant is started up.

The reaction mixture can comprise water in amounts within very wide limits. Thus, the mixture can comprise up to 50% by weight of water and even more. Preferably, the water content of the reaction mixture is between 2% and 15% by weight with respect to all the liquid constituents of the said mixture.

Preferably, the concentration of aminonitrile, diamine and dinitrile compounds in the reaction mixture is generally between 85% and 98% by weight with respect to all the liquid constituents of the said reaction mixture, with the exception of the ammonia, when it is present.

When the process of the invention is carried out continuously, the average composition will be determined by the ratio of the respective selectivities for aminonitrile and for diamine and by the rate of introduction of the dinitrile.

The amount of catalyst employed in the reaction mixture can vary very widely as a function, in particular, of the operating method adopted or of the reaction conditions chosen. Thus, if the dinitrile is gradually introduced into the reaction mixture, the catalyst/dinitrile to be hydrogenated ratio by weight will be much higher than if all the dinitrile is employed at the beginning of the reaction.

By way of indication, use may be made of 0.5% to 50% by weight of catalyst with respect to the total weight of the reaction mixture and generally of 1% to 35%.

The process of the invention is generally carried out at a reaction temperature of less than or equal to 150° C., preferably of less than or equal to 120° C. and more preferably still of less than or equal to 100° C.

In practical terms, this temperature is between ambient temperature (approximately 20° C.) and 100° C.

Prior to, simultaneously with or subsequent to the heating, the reaction chamber is brought to the appropriate hydrogen pressure, that is to say, in practice, between 1 bar (0.10 MPa) and 300 bar (30 MPa).

The duration of the reaction can vary as a function of the reaction conditions and of the catalyst.

In a batchwise operating method, it can vary from a few minutes to several hours.

It should be noted that a person skilled in the art can vary the order of occurrence of the stages of the process according to the invention, according to the operating conditions.

The other conditions which govern the hydrogenation (continuous or batchwise) in accordance with the invention relate to conventional technical arrangements known per se.

The examples which follow, given solely by way of indication, illustrate the invention.

In these examples, the following abbreviations are used:

ADN=adiponitrile

ACN=aminocapronitrile

HMD=hexamethylenediamine

DC=degree of conversion

S(ACN)=selectivity for ACN with respect to the starting substrate which has been converted (here, with respect to ADN).

EXAMPLE 1

Preparation of a Catalyst Formed of 5% Ru/1% Fe on a Y70 Acetylene Black Support 20 g of Y70 acetylene black, sold by SN2A, are charged to 800 ml of water. The suspension is heated to 90° C. with stirring. 1.8 g of $Na_2CO_3$, in a total of 70 ml of water, are added. After a period of 1 hour, a solution of 2.16 g of $RuCl_3$ hydrate in 120 ml of water is added. After 1 hour, a solution of 1 g of $FeCl_3$ hexahydrate in a total of 70 ml of water is run in and then, after a further hour, the mixture is allowed to cool to a temperature of 40° C. After filtration, the catalyst is washed with 4 times 200 ml of water at 40° C.

The catalyst is dried in an oven for 1 hour at 120° C. 21.3 g of catalyst are obtained.

Before testing, it is dried in an oven for 10 hours at 80° C. under reduced pressure.

EXAMPLE 2

Preparation of a Catalyst Formed of 5% Ru/0.5% Fe on Y200 Acetylene Black

The acetylene black support, sold by the company SN2A under the name Y200, is calcined beforehand under air for 1 hour at 500° C. 20 g of the calcined Y200 acetylene black are charged to 800 ml of water. The suspension is heated to 90° C. with stirring. 1.8 g of $Na_2CO_3$, in a total of 70 ml of water, are added. After a period of 1 hour, a solution of 2.16 g of $RuCl_3$ hydrate in 90 ml of water is added. After 1 hour, a solution of 0.51 g of $FeCl_3$ hexahydrate in a total of 70 ml of water is run in.

After 1 hour, the mixture is allowed to cool to a temperature of 40° C. After filtration, the catalyst is washed with 4 times 200 ml of water at 40° C.

The catalyst is dried in an oven for 1 hour at 120° C. 21.2 g of catalyst are obtained.

Before testing, it is dried in an oven for 10 hours at 80° C. under reduced pressure.

EXAMPLE 3

Preparation of a Catalyst Formed of 5% Ru/1% Fe on a Y200 Acetylene Black Support The Y200 acetylene black support is calcined beforehand under air for 1 hour at 500° C.

20 g of the calcined Y200 acetylene black are charged to 800 ml of water. The suspension is heated to 90° C. with stirring. 2 g of $Na_2CO_3$, in a total of 70 ml of water, are added. After a period of 1 hour, a solution of 2.16 g of $RuCl_3$ hydrate in 90 ml of water is added. After 1 hour, a solution of 1 g of $FeCl_3$ hexahydrate in a total of 70 ml of water is run in.

The mixture is allowed to cool to a temperature of 40° C.

After filtration, the catalyst is washed with 4 times 200 ml of water at 40° C.

The catalyst is dried in an oven for 1 hour at 120° C. 21.5 g of catalyst are obtained.

Before testing, it is reduced under hydrogen at a temperature rising from ambient temperature to 100° C. and is maintained for 4 hours at this temperature.

EXAMPLE 4

Hemihydrogenation of Adiponitrile

The following are charged to a reactor equipped with a stirrer, with means for introducing hydrogen and with a temperature regulation system:

| catalyst according to Example 1 | 2.4 g |
|---|---|
| ADN | 36 g |
| HMD | 36 g |
| 15N KOH in water | 5 g |
| water | 4.8 g |

The reaction mixture is heated to 80° C. after having purged the reactor with nitrogen and then with hydrogen; the pressure is regulated at 2.5 MPa at this temperature by continuous addition of hydrogen. The progress of the reaction is monitored by the consumption of hydrogen and the analysis by gas chromatography (GC) of a withdrawn sample of the reaction mixture.

The following results are obtained:

| reaction time: | 105 min |
|---|---|
| DC of the ADN: | 67% |
| S(ACN) | 75% |

EXAMPLE 5

Hemihydrogenation of Adiponitrile

The following are charged to a 150 ml reactor equipped with a stirrer, with means for introducing hydrogen and with a temperature regulation system:

| catalyst according to Example [lacuna] | 21.5 g |
|---|---|
| ADN | 22 g |
| HMD | 22 g |
| 15N KOH in water | 3.1 g |
| water | 3 g |

The reaction mixture is heated to 80° C. after having purged the reactor with nitrogen and then with hydrogen; the pressure is regulated at 2.5 MPa at this temperature by continuous addition of hydrogen. The progress of the reaction is monitored by the consumption of hydrogen and the analysis by gas chromatography (GC) of a withdrawn sample of the reaction mixture.

The following results are obtained:

| reaction time: | 90 min |
|---|---|
| DC of the ADN: | 85% |
| S(ACN) | 73% |

EXAMPLE 6

Hemihydrogenation of Adiponitrile in the Presence of $NH_3$

The following are charged to a 300 ml reactor equipped with a stirrer, with means for introducing hydrogen and with a temperature regulation system:

| catalyst according to Example 3 | 4 g |
|---|---|
| ADN | 42.5 g |
| water | 10.6 g |
| $NH_3$ | 64.4 g |

The reaction mixture is heated to 80° C. after having purged the reactor with nitrogen and then with hydrogen; the pressure is regulated at 11 MPa at this temperature by continuous addition of hydrogen. The progress of the reaction is monitored by the consumption of hydrogen and the analysis by gas chromatography (GC) of a withdrawn sample of the reaction mixture.

The following results are obtained:

| reaction time: | 300 min |
|---|---|
| DC of the ADN: | 57% |
| S(ACN) | 82% |

Comparative Example A

Hemihydrogenation of Adiponitrile

The following are charged to a 300 ml reactor equipped with.a stirrer, with means for introducing hydrogen and with a temperature regulation system:

| Raney Ni (doped with iron and chromium) | 3 g |
|---|---|
| water | 13.5 g |

-continued

| | |
|---|---|
| 1N KOH in water | 1.5 g |
| ADN | 67.5 g |
| HMD | 67.5 g |

The reaction mixture is heated to 50° C. after having purged the reactor with nitrogen and then with hydrogen; the pressure is regulated at 2.2 MPa at this temperature by continuous addition of hydrogen. The progress of the reaction is monitored by the consumption of hydrogen and the analysis by gas chromatography (GC) of a withdrawn sample of the reaction mixture.

The following results are obtained:

| | |
|---|---|
| reaction time: | 15 min |
| DC of the ADN: | 66% |
| S(ACN) | 80% |

Comparative Example B

Hemihydrogenation of Adiponitrile

The following are charged to a 180 ml reactor equipped with a stirrer, with means for introducing hydrogen and with a temperature regulation system:

| | |
|---|---|
| catalyst formed of 5% Ru on an active charcoal support sold by Engelhard under the name Escat 40 | 2.4 g |
| ADN | 36 g |
| HMD | 36 g |
| 15N KOH in water | 0.9 g |
| water | 8.8 g |

The catalyst was reduced beforehand under hydrogen at a temperature rising from ambient temperature to 500° C. and was maintained for 4 hours at this temperature.

The reaction mixture is heated to 80° C. after having purged the reactor with nitrogen and then with hydrogen; the pressure is regulated at 2.5 MPa at this temperature by continuous addition of hydrogen. The progress of the reaction is monitored by the consumption of hydrogen and the analysis by gas chromatography (GC) of a withdrawn sample of the reaction mixture.

The following results are obtained:

| | |
|---|---|
| reaction time: | 120 min |
| DC of the ADN: | 73% |
| S(ACN) | 36% |

What is claimed is:

1. A process is provided for the hemihydrogenation of dinitriles to corresponding aminonitriles using hydrogen in the presence of a supported catalyst, wherein the supported catalyst comprises ruthenium supported on a carbon black, called acetylene black, resulting from the pyrolysis of paraffin oils.

2. The process according to claim 1, wherein the catalytic system comprises at least one doping element, at least one of which is iron.

3. The process according to claim 2, wherein the concentration of doping element with respect to the ruthenium is between 5% and 60% by weight.

4. The process according to claim 1, wherein the catalyst is subjected to reduction prior to its use.

5. The process according to claim 2, wherein the doping elements other than iron are selected from the group consisting of tungsten, manganese, rhenium, zinc, cadmium, lead, aluminium, tin, phosphorus, arsenic, antimony, bismuth, silicon, titanium, zirconium, the rare earth metals, palladium, platinum, iridium, osmium, copper, silver, chromium and molybdenum.

6. The process according to claim 1, wherein the starting hydrogenation mixture comprises ammonia.

7. The process according to claim 1, wherein the starting hydrogenation mixture comprises a strong inorganic base selecting from the group consisting of alkali metal or alkaline earth metal hydroxides, carbonates and alkoxides as well as hydroxides, carbonates and alkoxides of the ammonium cation.

8. The process according to claim 7, wherein the strong inorganic base employed is selected from the group consisting of the following compounds: LiOH, NaOH, KOH, RbOH, CsOH and their mixtures.

9. The process according to claim 7, wherein the amount, expressed in moles of OH$^-$, of inorganic base present in the reaction mixture is between 0.1 mol per kilogram of catalyst and 50 mol/kg.

10. The process according to claim 1, wherein the aliphatic dinitriles which can be employed in the process of the invention are the dinitriles of general formula (I):

NC—R—CN     (I)

in which R represents a linear or branched alkylene or alkenylene group having from 1 to 12 carbon atoms.

11. The process according to claim 1, wherein the concentration of the targeted aminonitrile and/or of the corresponding diamine and of the unconverted dinitrile in the reaction mixture is between 80% and 99.5% by weight with respect to all the liquids present in said reaction mixture, with the exception of the ammonia, when it is present.

12. The process according to claim 1, which is carried out at a reaction temperature of less than or equal to 150° C.

13. The process according to claim 1, which is carried out at a hydrogen pressure of between 1 bar (0.10 MPa) and 300 bar (30 MPa).

14. The process according to claim 7, wherein the strong inorganic base comprises alkali metal hydroxides, carbonates and alkoxides and compounds comprising a quaternary ammonium radical.

15. The process according to claim 9, wherein the amount of inorganic base present in the reaction mixture is between 5 and 35 mol per kilogram of catalyst.

16. The process according to claim 10, wherein R represents a linear or branched alkylene radical having from 2 to 6 carbon atoms.

17. A process for hemihydrogenating a dinitrile to form an aminonitrile, comprising:

reacting a dinitrile with hydrogen in the presence of a catalyst to produce an aminonitrile, wherein the catalyst comprises ruthenium on a support comprising acetylene black.

* * * * *